United States Patent
Hoogenboom et al.

(10) Patent No.: US 10,132,753 B2
(45) Date of Patent: Nov. 20, 2018

(54) METHOD AND APPARATUS FOR DETERMINING A DENSITY OF FLUORESCENT MARKERS IN A SAMPLE

(71) Applicant: DELMIC B.V., Delft (NL)

(72) Inventors: Jacob Pieter Hoogenboom, Delft (NL); Pieter Kruit, Delft (NL)

(73) Assignee: DELMIC B.V., Delft (NL)

( * ) Notice: Subject to any disclaimer, the term of this patent is extended or adjusted under 35 U.S.C. 154(b) by 0 days.

(21) Appl. No.: 15/116,788

(22) PCT Filed: Feb. 6, 2015

(86) PCT No.: PCT/NL2015/050080
§ 371 (c)(1),
(2) Date: Aug. 4, 2016

(87) PCT Pub. No.: WO2015/119502
PCT Pub. Date: Aug. 13, 2015

(65) Prior Publication Data
US 2016/0377544 A1    Dec. 29, 2016

(30) Foreign Application Priority Data
Feb. 6, 2014 (NL) .................................... 2012218

(51) Int. Cl.
*G01N 25/02* (2006.01)
*G01N 21/64* (2006.01)
*H01J 37/22* (2006.01)

(52) U.S. Cl.
CPC ..... *G01N 21/6456* (2013.01); *G01N 21/6428* (2013.01); *H01J 37/228* (2013.01);
(Continued)

(58) Field of Classification Search
CPC ........... G01N 21/6428; G01N 21/6458; G01N 21/64; G01N 21/6408; G01N 2021/6421
See application file for complete search history.

(56) References Cited

U.S. PATENT DOCUMENTS

| 2006/0098188 A1* | 5/2006 | Buijsse | G01N 21/6428 356/72 |
| 2012/0193530 A1* | 8/2012 | Parker | H01J 37/228 250/307 |
| 2015/0108350 A1* | 4/2015 | Hoogenboom | H01J 37/22 250/307 |

FOREIGN PATENT DOCUMENTS

| EP | 1655597 | 5/2006 |
| EP | 2482061 | 8/2012 |
| WO | WO-2013151421 | 10/2013 |

OTHER PUBLICATIONS

O'Haver "Derivative Spectroscopy and its Applications in Analysis" Derivative Spectroscopy Anal. Proc. Jan. 1, 1982, p. 23-46.*
(Continued)

*Primary Examiner* — David Porta
*Assistant Examiner* — Mamadou Faye
(74) *Attorney, Agent, or Firm* — Womble Bond Dickinson (US) LLP (57) ABSTRACT

The invention provides a method of determining a measure of a density of markers in a sample, and an apparatus arranged for performing said method. In particular said method comprising the steps of:
  irradiating an illumination region of the sample with light, wherein the markers present in the illumination region of the sample emit fluorescence light in response to the irradiation with light,
  detecting an intensity of the fluorescence light from a detection region of the sample, comprising at least a part of said the illumination region,
  irradiating an area within said detection region of the sample with a focused charged particle beam to deposit a dose of charged particles in said area, and
  determining a measure of the density of markers in said area using a change of the detected intensity of the
(Continued)

fluorescence light as a function of the deposited dose of charged particles in said area.

22 Claims, 7 Drawing Sheets

(52) U.S. Cl.
CPC ............... *G01N 2021/6441* (2013.01); *G01N 2201/105* (2013.01)

(56) References Cited

OTHER PUBLICATIONS

International Search Report, dated Apr. 22, 2015, Application No. PCT/NL2015/050080.
Zonnevylle, A. C., et al., "Integration of a high-NA light microscope in a scanning electron mircoscope", *Journal of Microscopy*, vol. 252, Issue 1, (Jul. 25, 2013), 58-70.

\* cited by examiner

METHOD AND APPARATUS FOR DETERMINING A DENSITY OF FLUORESCENT MARKERS IN A SAMPLE

BACKGROUND

The invention relates to a method of determining at least a measure of a density of markers in a sample.

Fluorescence microscopy is an important imaging method for biological and bio-medical sciences because functional biological molecules like proteins can be visualized through the attachment of a marker. Such a marker is a small fluorescent molecule that, upon illumination with light of a specific color, emits light of a slightly different color and that can be attached to a protein of interest. By filtering the illumination light, the marked proteins become visible onto a dark background. The marker molecule can be of non-biological origin (i.e. exogenous), in which case it can be linked to biological molecules via a linker molecules such as anti-bodies. This is usually referred to as immuno-labelling. Alternatively, the maker molecule can be genetically expressed, in which case it is already present in the biological material itself, i.e. endogenous. These fluorescent markers mostly belong to the class of fluorescent proteins. In most cases the function of a protein or of a group of proteins is intricately linked to the biological structure onto which the protein is attached. Such structures can be microtubules, fibers, mitochondria, organelles, the nucleus, particles, etc. In a biological cell, these structures typically have one or more dimensions that are below the diffraction limit for optical microscopy, i.e. smaller than 300 nm.

In principle, the position of a fluorescent molecule can be retrieved at much higher accuracy than that imposed by the diffraction limit. Localization accuracy down to about 20 nm has been reported, provided one or only a few fluorescent molecules are contained within an area equal to the size of the diffraction-limited spot. The localization procedure is done through data analysis of the measured optical intensity gradient (de-convolution with the optical Point Spread Function, Gaussian fitting).

In case more than a single molecule is located within the diffraction-limited spot their individual positions can still be retrieved provided that discrete bleaching of each individual molecule can be observed in the recorded optical intensity. Bleaching refers to a change in the fluorescent molecule that makes the molecule non-fluorescent. This bleaching can also be caused by an induced destruction of a fluorescent molecule, e.g. through irradiation by a focused particle beam.

Such a method with induced destruction is for example disclosed in the European Patent Application 1.655.597. This patent application describes a method of determining the position of fluorescent markers in a sample with a high spatial resolution. To this end, the sample is illuminated with a light beam, while the sample is simultaneously scanned by a particle beam. In response to the excitation by the light beam, a flux of fluorescence radiation is emitted from the sample. This flux is generated by one or more markers in the sample that are located in the illuminated region. During scanning, markers will be impinged upon by the particle beam and will be damaged in such a manner that the marker impinged upon will no longer emit fluorescent radiation. This leads to a reduction of the flux of fluorescent radiation. This reduction is detected. If the flux that results from excitation decreases by at least a previously determined threshold value, this has to be because a marker in the excitation region is damaged by the particle beam. Since the position of the particle beam with respect to the sample is known at the moment that the marker is damaged, the position of the marker in the sample is, accordingly, also known.

The same procedure of identifying the location of individual markers by determining damage events which are represented by a vertical drop in the fluorescence signal, is also described in EP 2.482.061. In EP 2.482.061 it is described that this method can also be done in a scan field containing 10000 green fluorescent proteins (GFPs), although the distinguishing of individual GFP damage events from out of the overall statistical noise in the light signal will be more difficult when compared with a sample having less GFPs, for example 100 GFPs, in the scan field.

As the discrete individual bleaching steps have to be observed above the background of the remaining fluorescent molecules, localization is typically limited to marker densities of 15-20 molecules per diffraction area. For higher densities the detection of a signal of a single molecule in view of the noise in the signal from other molecules, is very difficult.

However as proteins involved in a biological reaction assemble at a biological structure with one or more dimensions in the 10-100 nm size range, the local density of fluorescent markers is typically much higher than that allowed for localization techniques that rely on discrete bleaching steps as for example described in European Patent Applications 1.655.597 and 2.482.061. In a structure of interest there are usually so many fluorescent markers that it is impossible to identify the signal from a single marker in the total fluorescence signal within the diffraction spot. In addition, in real life samples, the total numbers of fluorescent makers in a scan field is not known upfront, as is the case in the examples described in EP 2.482.061.

A further disadvantage for using the method as described in EP 2.482.061 is, that every marker in the scan field is destroyed by scanning the charged particle beam over the same area as irradiated by the laser beam. The part of the sample which has been scanned by the charged particle beam is therefore permanently damaged and cannot be used for further fluorescence measurements.

It is the aim of the present invention to provide an alternative and novel technique for studying fluorescent markers in a sample.

SUMMARY OF THE INVENTION

According to a first aspect, the invention provides a method of determining at least a measure of a density of markers in a sample, comprising the steps of:

irradiating an illumination region of the sample with light, wherein the markers present in the illumination region of the sample emit fluorescence light in response to the irradiation of the sample with light, detecting an intensity of the fluorescence light from a detection region of the sample, comprising at least a part of said the illumination region, irradiating an area within said detection region of the sample with a focused charged particle beam to deposit a dose of charged particles in said area, and determining a measure of the density of markers in said area using a change of the detected intensity of the fluorescence light as a function of the deposited dose of charged particles in said area.

The novel method of the present application is based on the insight that, contrary to the approach as described in European Patent Application 1.655.597, it is not strictly necessary to determine the exact position of all individual markers, but rather the local density of the markers in the sample is relevant. This local density should be determined at the best resolution possible. With charged particle beam irradiation, the fluorescence from markers can be modified at a spatial resolution of the charged particle beam probe size, which in principle can go below 5 nm. The intensity of the fluorescence light is measured by an optical detector which provides a fluorescence signal which preferably is proportional to said intensity. By monitoring the change of the intensity of the fluorescence light as a function of the deposited dose of charged particles at a certain location, the local number density of the markers at said location can be obtained without the need to locate individual markers or to separate the discrete fluorescence signals from the individual markers.

It is noted that the change of the intensity of the fluorescence light may be a decrease or an increase of intensity depending on the interaction between the markers and the charged particles from said charged particle beam.

It is further noted that in order to determine a changed of the intensity of the fluorescence light as a function of the deposited dose of charged particles at a certain location can be done without having to destroy all markers in said location.

In an embodiment, said method comprises the step of determining the derivative of the fluorescence signal as a function of the deposited dose of charged particles. This derivative provides a measure for the density of markers at said location.

In an embodiment, said method further comprising the step of determining a rate of change of the intensity of the fluorescence light, preferably in combination with depositing a substantial constant current of charged particles. Because of the use of a constant current of charged particles, the measure for the density of markers at said location can be obtained by determining the derivative of the fluorescence signal as a function of time.

In an embodiment, the detection region is substantially centered around the area irradiated by the focused charged particle beam.

In an embodiment, the focused charged particle beam is scanned over at least a part of the sample, wherein at multiple positions in said at least a part of the sample a measure of the density of marker is determined, and wherein said measure of the density as determined at said multiple positions is used to produce an image of the density distribution of said markers in said part of the sample. By scanning the charged particle beam over the sample, at each position a certain dose is deposited and the change in fluorescence light in the area around the particle beam is measured and contributed to the position of the particle beam. Thus a whole image can be built up wherein each pixel of the image corresponds, for example, to a position on or in the sample. At each position at least a measure for the density of markers can be obtained from the change in fluorescent light as measured and this density is represented at the corresponding pixel in the image. It is noted that the whole image can be built up with the resolution of the charged particle beam.

An interesting aspect of this imaging method is that the resolution is determined by the size of the charged particle beam, while the signal to noise ratio is determined by the fluorescence signal. The signal to noise can, for example, be improved by using a low current in the charged particle beam so that there is a lot of time to collect signal in the fluorescence image.

In an embodiment, the part of the sample over which the focused charged particle beam is scanned, is at least substantially arranged within said detection region. In an embodiment, during said scanning, the intensity of the fluorescence light is detected from substantially the same detection region of the sample. An advantage of this embodiment is, that the population of markers in the detection region does not change during said scanning and that a changed in the intensity of the fluorescence light is not due to a change in the population of markers in the detection region, but predominantly due to the interaction of the charged particle beam with the markers in said area irradiated by the focused charged particle beam.

In an alternative embodiment, a center of the detection region on the sample is scanned together with the focused charged particle beam. The detection region in which the change of the intensity of the fluorescence light is measured, is preferably centered around the position of the charged particle beam, and this centered position of the charged particle beam with respect to the detection region from which the fluorescence light is measured is maintained during the scanning. Thus the alignment of the optical fluorescence microscope and the charged particle microscope is substantially constant. In an embodiment, during said scanning, the sample is moved with respect to the optical fluorescence and the charged particle microscope. An advantage of this embodiment is, that the part of the sample which is scanned can be much larger than the detection region.

However, there may be a limit to the number of photons a marker can emit before it bleaches as a result of the light illumination. In that case, the method for obtaining a image according to the method of the present invention can be optimized using one or more of the following method steps:

i. The scanning of the charged particle beam over at least the part of the sample is repeated to obtain subsequent scans, wherein the results of the subsequent scans are added. A first image can be collected with low signal to noise ratio. If after one scan the change in fluorescence is not yet saturated, a second san can be made to increase the signal to noise, etcetera.

ii. Also, just as in normal imaging, the signal in neighboring pixels may be added so as to increase the signal to noise, at the cost of resolution.

iii. Alternatively, if it is known in advance that there is not sufficient signal to noise, the size of the charged particle beam can be chosen larger. This will increase the relative change in fluorescence signal, at the cost of resolution.

These possibilities: adding different images, averaging pixels to increase the signal to noise, and choosing a variable resolution, are very different from a situation in which there are a few markers dispersed over the surface, which are either on or off, as described in European Patent Application 1.655.597.

In an embodiment of item i. above, the scanning is repeated to obtain subsequent scans, wherein for each scan the intensity of the fluorescence light is measured once per position of the charged particle beam and is used to produce one image per scan, wherein said image represents the effect of deposition of a substantially constant dose per position in said image, wherein said images of the subsequent scans are combined to produce an image of the density distribution of said markers in said part of the sample. An advantage of this embodiment is that for each scan an image is produced, and in case the signal to noise ratio in an image from said first scan is too low, an additional scan can be made and the additional image is combined to produce an image with a better signal to noise ratio. The performing of additional scans and adding of images can be stopped when a desired or minimum signal to noise ratio has been reached. Thus the number of scans can be limited to the number required to reach the desired or minimum signal to noise ratio.

In an alternative embodiment, the scanning is repeated to obtain subsequent scans, wherein for each scan the intensity of the fluorescence light is measured once per position of the charged particle beam, wherein each measurement represents the effect of deposition of a substantially constant dose per position, wherein the measurements of the subsequent scans are combined, and these combined measurement are used to produce an image of the density distribution of said markers in said part of the sample. An advantage of this embodiment is that the image is produced after the measurements of the subsequent scans have been carried out and have been combined. Thus it is not necessary to produce an image for each scan, which may result in a faster acquisition of data, at least when compared to the previous embodiment.

In an embodiment, a position of the sample where a dose of charged particles is deposited and where the change in the intensity of the fluorescence light is measured, is selected based on the intensity of the fluorescence light as measured before a dose of charged particles is deposited. An advantage if this embodiment is, that the parts of the sample in which the method of the present invention can be applied, can be pre-selected without reducing the fluorescence signal by an interaction between the markers and the charged particles from said charged particle beam.

In an embodiment, the detection region in which the intensity of the fluorescence light is measured is scanned over at least a part of the sample, wherein a first scan is obtained without the charged particle beam irradiating the sample and a second scan is obtained with the charged particle beam irradiating the sample, and wherein variations in the intensity of the fluorescent light as measured during the scanning of the detection region in the first scan are used to compensate for variations in the intensity of the fluorescent light as measured during the scanning of the detection region in the second scan. In an embodiment, variations in the intensity of the fluorescent light as measured during the scanning of the detection region in the first scan are subtracted from the intensity of the fluorescent light as measured during the scanning of the detection region in the second scan. In an embodiment two images are obtained, a first image obtained during the first scan and a second image obtained during the second scan, and the first image is subtracted from the second image. Due to this compensation, in particular this subtraction, a noise contribution from areas where there is no signal is reduced.

In an embodiment, the sample is imaged onto a pixelated detector or camera, in particular a CCD camera or a CMOS camera, and wherein said detecting an intensity of the fluorescence light from a detection region of the sample is obtained by filtering the image information from said detector or camera in order to obtain only information from at least substantially the detection region. This embodiment provides a way to reduce the noise contribution from areas, in particular areas on the detector or camera, where there is no relevant signal.

In an embodiment, the position of the focused charged particle beam on the sample is at least substantially stationary between two subsequent read outs of said detector or camera. Advantageously the effect of the focused charged particle beam in each of said subsequent read outs can be added or subtracted, for example to improve a signal to noise ratio in an image formed by said read outs.

In an embodiment, the position of the focused charged particle beam is varied over multiple substantially separate positions on the sample between two subsequent read outs of said detector or camera, wherein a separation between said separate positions on the sample is substantially equal or larger than the size of said detection region. Advantageously the effect of the focused charged particle beam(s) at multiple substantially separate positions can be evaluated with substantially one read out or with one image formed by said read out. Accordingly a density distribution or an image thereof can be created faster and/or from a larger area on the sample.

In an embodiment, the intensity of the fluorescence light is measured through an aperture in a conjugate plane of the sample. An advantage of such a set-up is, that the detection region or detection volume from which the fluorescent light is detected, can be reduced. Preferably a confocal microscope is used in this embodiment.

In an embodiment, a size and/or position of illumination region on the sample is determined by an aperture in a conjugate plane of the sample.

According to a second aspect, the present invention provides an inspection apparatus for determining at least a measure of a density of markers in a sample, said inspection apparatus comprising in combination:

an optical microscope arranged for irradiating an illumination region of the sample with light, wherein the markers present in the illumination region of the sample emit fluorescence light in response to the irradiation of the sample with light, and for detecting an intensity of the fluorescence light from a detection region of the sample, wherein said detection region comprising at least a part of said illumination region;

an ion- or electron microscope arranged for irradiating an area within said detection region of the sample with a focused charged particle beam, wherein said focused charged particle beam preferably has a cross section that is smaller than a cross section of said detection region; and a data processing system adapted to construct an image of a distribution of markers in the sample, wherein said image is constructed using or calculating a measure of the density of the markers at various locations in or on said sample as obtained using the method or any one of the embodiments thereof as described above.

According to a third aspect, the present invention provides a computer program having instructions adapted to construct an image of a distribution of markers in a sample provided with said markers, wherein said image is constructed using or calculating a measure of the density of the markers at various locations in or on said sample using the method or any one of the embodiments thereof as described above.

According to a fourth aspect, the present invention provides a computer readable medium, having recorded thereon a computer program as described above.

The various aspects and features described and shown in the specification can be applied, individually, wherever possible. These individual aspects, in particular the aspects and features described in the attached dependent claims, can be made subject of divisional patent applications.

BRIEF DESCRIPTION OF THE DRAWINGS

The invention will be elucidated on the basis of an exemplary embodiment shown in the attached drawings, in which.

DETAILED DESCRIPTION OF THE INVENTION

The present invention aims to provide at least a measure for the density of markers in a sample, contrary to the approach as described in EP 1 655 597 which determines the exact positions of individual markers in a sample.

This density of markers, or a measure thereof, should be determined at the best resolution possible. For example, when using electron-beam irradiation, the fluorescence from markers can be modified at a resolution determined by the size of the electron beam on the sample. In principle, an electron beam can be focused down to a size below 5 nm.

Figure 1:
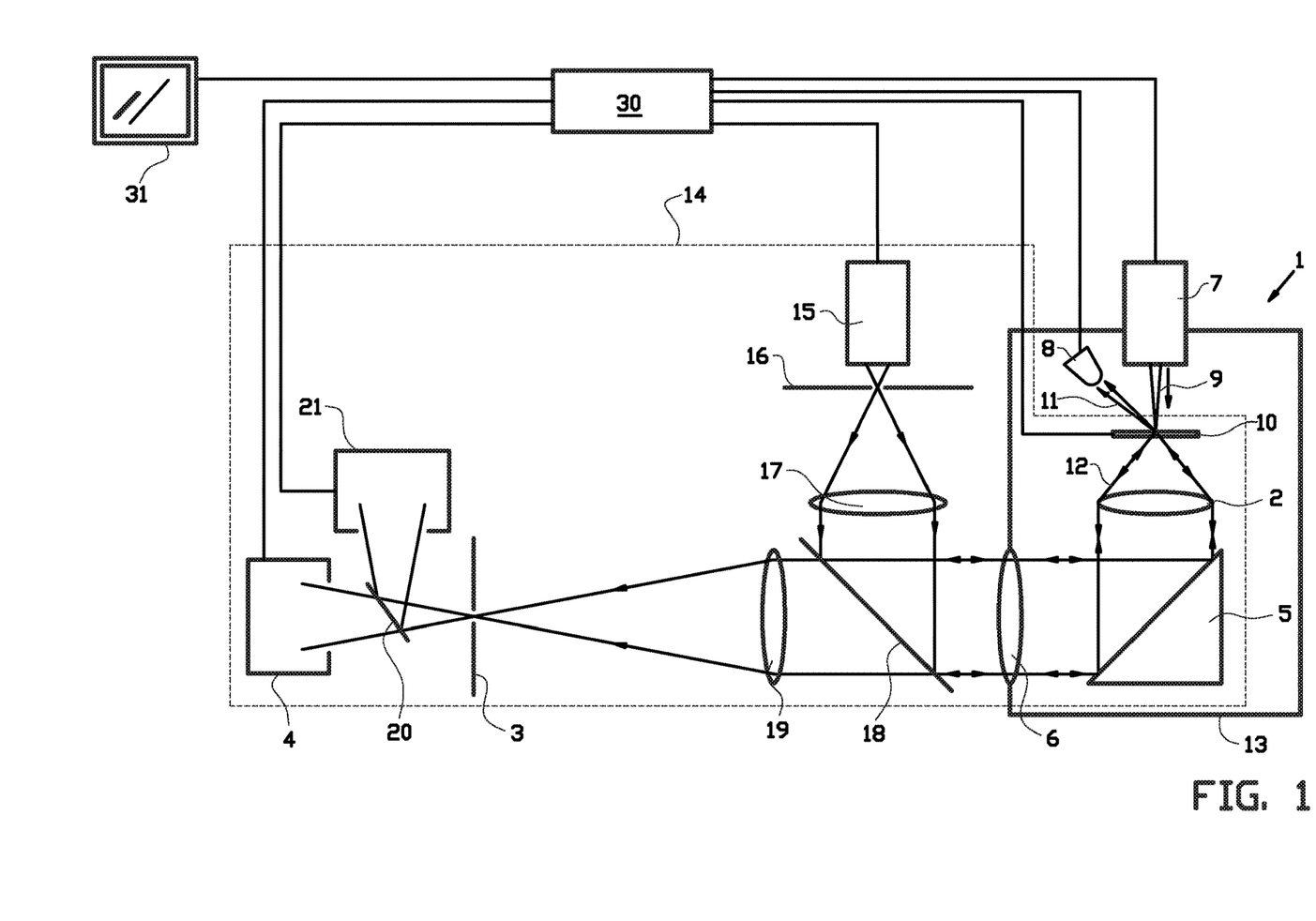
FIGS. 1 and 2 schematically depict a basic design of an apparatus as typically used by the present invention.

By way of example, a typical set up for performing the method of the present invention is shown in FIG. 1. FIG. 1 shows a so-called optical SEM combination. It comprises in combination at least an optical microscope 2, 3, 4 and a charged particle microscope 7, 8, such as an ion- or electron microscope. This example however by no means excludes any known or yet unknown variation or alternative thereof.

With reference first to FIG. 1, the basic design of a first example of an inspection apparatus 1 of the invention is explained. FIG. 1 represents the inspection apparatus 1 of an embodiment which is provided with a light source 15 (for instance a laser) and ancillary means for directing light from the light source 15 to the sample 10 for irradiating an illumination region of the sample 10. In the following discussion use will be made of a laser source 15 as a light source, but other light sources may also be applied.

The ancillary means for directing the light of the laser source 15 to the sample 10 comprises a pinhole 16, a collimating lens 17, a dichroïc mirror 18 to project the light from the laser source 15 into the beam path of the optical microscope 2, 3, 4. The light from the laser source 15 then traverses through the optical window 6, is redirected towards the sample 10 by a mirror 5 and is focused onto the sample by an objective lens 2 in order to irradiate an illumination region of the sample 10.

If there are markers present in said illumination region which can be excited by the laser light, these markers will emit luminescence or fluorescence light in response to the irradiation of the sample 10 with light from the laser source 15. Such markers can be referred to as emitters.

The emitted luminescence of fluorescence light is collected and detected by the optical microscope 2, 3, 4. It is noted that the fluorescence light 12 and the light from the laser source 15 travel in the opposite directions in the beam path of the optical microscope. The optical microscope 2, 3, 4 is equipped with an light collecting device to receive in use luminescence or fluorescence light 12 emitted by the sample 10 and to focus it on a photon-detector 4. The light collecting device as shown in FIG. 1 comprises an objective lens 2, however also a mirror or a glass fiber can be used as a light collecting device. The fluorescence light 12 that is induced by the light source originating from the light source 15 travels back and exits the vacuum chamber 13 through the optical window 6. After passing the dichroic mirror 18 and the lens 19, the luminescence light passes the pinhole 3 and arrives at the photon-detector 4. Optionally a beam splitter 20 may be applied in combination with a spectrometer 21 for further analysis. Other or multiple detection paths may be also be used.

In the present example the optical microscope 2, 3, 4 is of an confocal type having a pinhole 3 which is arranged in a conjugate plane of the sample 10, between the objective lens 2 and the photon detector 4.

In addition, the inspection apparatus 1 comprises a charged particle microscope 7, 8 comprises a source 7 for emitting a primary beam 9 of charged particles to the sample 10, which is preferably supported by a substrate included in a sample holder (not shown in detail). The apparatus comprises a detector 8 for detecting:

charged particles 11 which are scattered back from the sample 10, or emitted, transmitted, or scattered secondary charged particles or radiation from the sample 10 which are induced by the primary beam 9.

As schematically shown in FIG. 1, the charged particle microscope 7,8 is substantially arranged inside a vacuum chamber 13. The optical microscope 2, 3, 4 is placed partially inside and partially outside said vacuum chamber 13. The dashed line 14 encircles those parts of the inspection apparatus 1 of the invention that may all or some of them be mounted on a (replaceable) door of the vacuum chamber 13. In particular, the sample holder for the sample 10, the light collecting device 2, the optional pinhole 3, and the photon-detector 4, are preferably mounted on said door of the vacuum chamber 13. Preferably this also entails the laser source 15 and the ancillary means that are used as explained above for directing light to the sample 10 and excite it to emit luminescence light which is detectable by the optical microscope. This particular construction enables an easy retrofit or completion of an existing charged particle microscope according to prior art in order to convert it into an inspection apparatus according of the integrated type as used in the present invention.

As described above, if there are emitters present in the region illumination by the laser light, these emitter will emit luminescence or fluorescence light in response to the irradiation of the sample 10 with light from the laser source 15. When the primary beam 9 of charged particles originating from the source 7 of the ion- or electron microscope 7, 8 is scanned through the spot of the sample were said emitters are located, some emitters may switch off (or be modified) due to the action of the primary beam which leads to a modification of the fluorescence signal originating from the sample 10. This modification is measured by the photon-detector 4. By measuring the changed of the fluorescence signal as a function of the deposited dose of charged particles, a measure for the density of the emitters at the position where the primary beam 9 is located on the sample. Thus the position and density of emitters at said position can be determined at an improved resolution to a value in the range of 1 nm, similar to the resolution of an ion- or electron microscope. Measurements can be carried out in several manners, for instance by having the primary beam 9 of radiation and the light originating from the light source 15 illuminate the sample 10 simultaneously or with a preselected time-delay.

In FIG. 1, a processing unit 30, alternatively denoted controller, is provided and useable as an automation unit, e.g. in the form of a computer, including a personal computer provided with dedicated software, implementing one or more methods of use of the inspection apparatus. The controller 30 is e.g. used to control the working of the charged particle microscope 7, 8, the movement of sample holder 10, and the optical microscope 4, 15, 21, and is provided with a computer program having instructions adapted to construct an image of a distribution of markers in the sample 10 provided with said markers, wherein said image is constructed using or calculating a local density of the markers at various locations in or on said sample as obtained from measuring a change of the intensity of the fluorescence light as a function of the deposited dose of charged particles at said location according to the method as described in more detail below.

The controller 30 may typically be provided with one or more screens 31, e.g. one screen or screen part for depicting the recorded optical image, another screen or another part of the same screen depicting an image, in particular of the same object, i.e. substrate, recorded via the charged particle part of the inspection apparatus, and another screen or another part of the same screen depicting an image of a distribution of markers in the sample 10 as constructed by the computer program.

Figure 2:
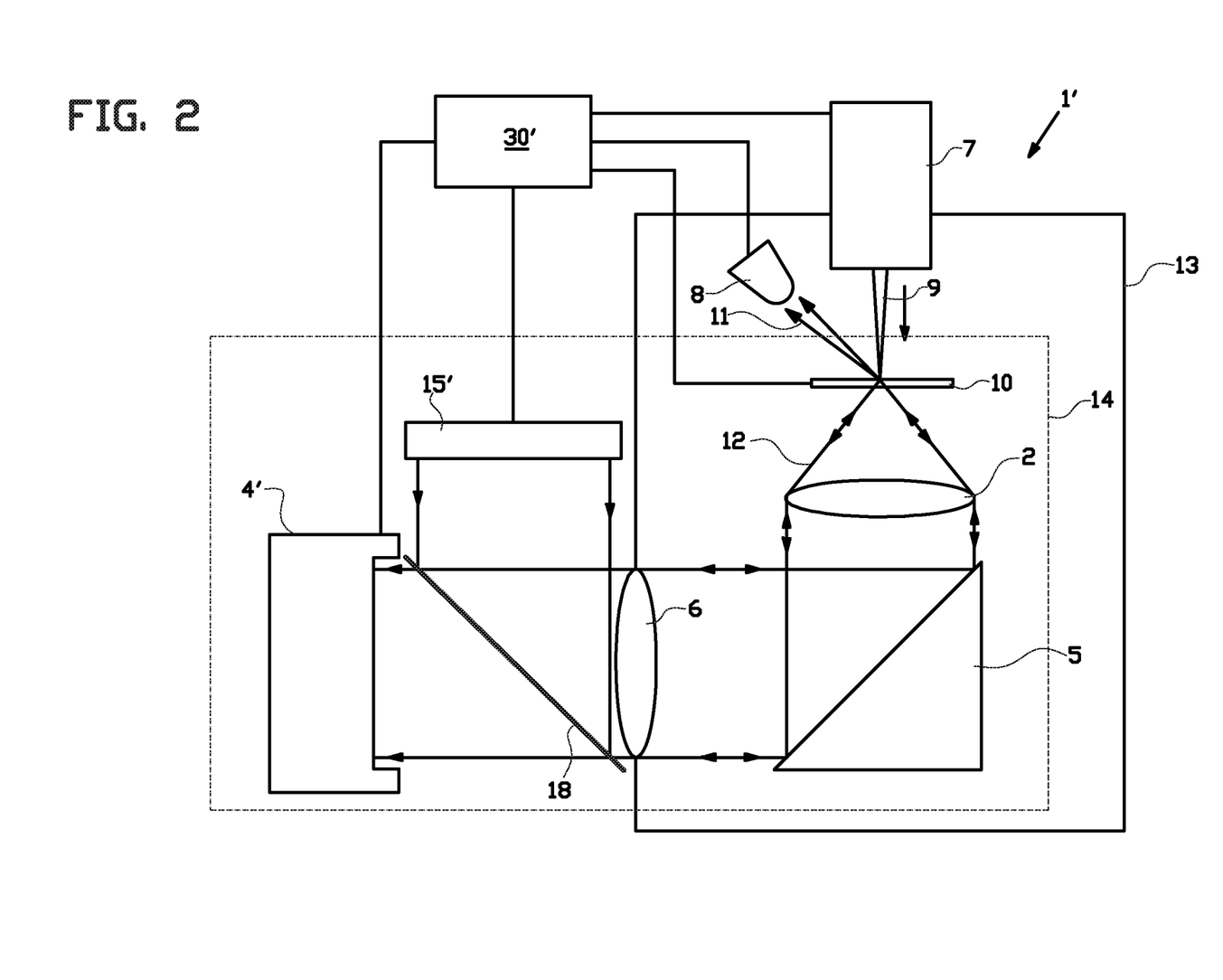

In a second example, as shown in FIG. 2, the inspection apparatus 1' comprises a light source 15' for illuminating an area of the sample 10, and a camera 4' for collecting an image, also denoted a wide field image, of the illuminated area of the sample 10. The camera 4' is for example a CCD camera which can be controlled by the controller 30', which also controls the charged particle microscope 7, 8, the movement of the sample holder 10, and the light source 15'.

Example of the Method of the Invention for a Single Point Measurement

Figure 3A:
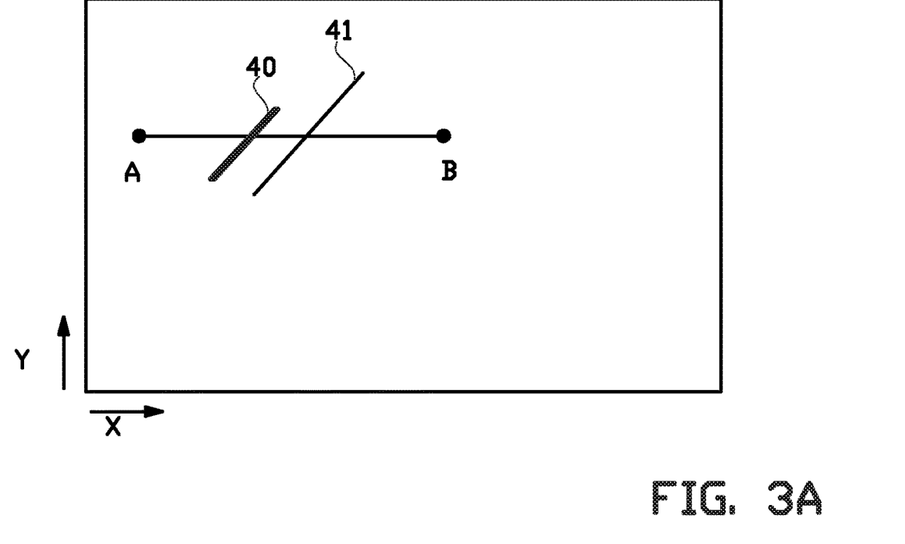
FIG. 3A schematically shows a distribution of fluorescent markers is a sample.
Figure 3B:
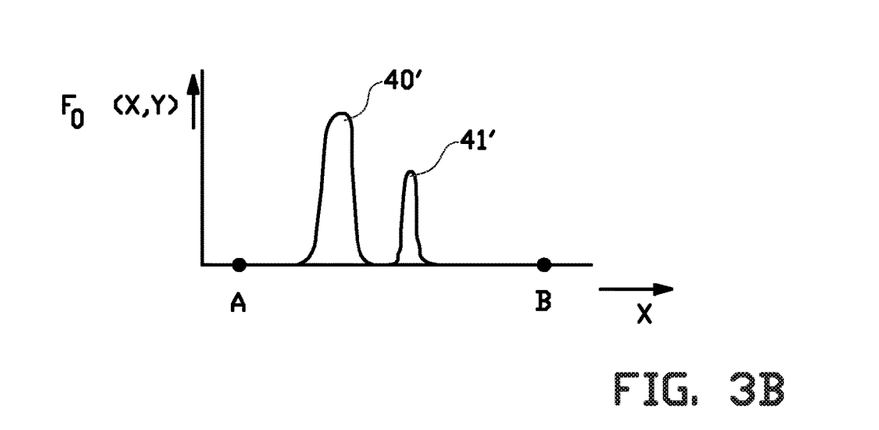
FIG. 3B schematically shows the distribution of the fluorescent markers as a function of the position along the line A-B in FIG. 3A.

In this example, a sample 10 is provided in the setup of FIG. 1 for example, which sample 10 contains a distribution of fluorescent markers 40, 41 as shown in FIG. 3. When moving along the line A-B the distribution of the fluorescent markers as a function of the position is schematically depicted in FIG. 3A. The distribution of fluorescent markers $F_0(X,Y)$ shows two peaks 40', 41' as schematically shown in FIG. 3.

Figure 4A:
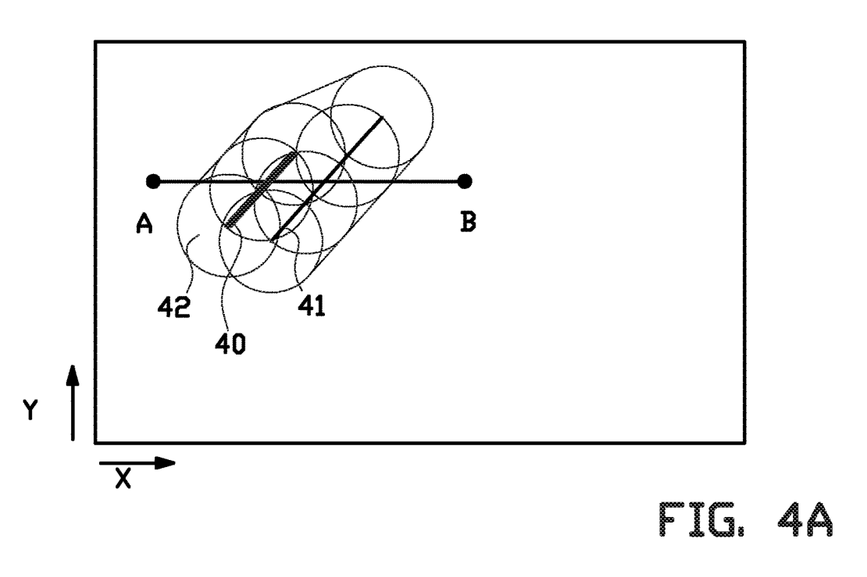
FIG. 4A schematically shows the fluorescence image of the sample of FIG. 3A.
Figure 4B:
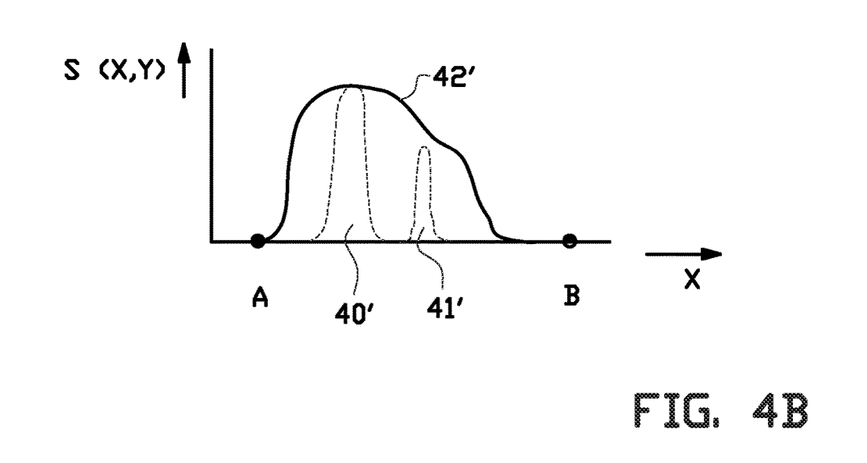
FIG. 4B schematically shows a fluorescence signal as a function of the position along the line A-B in FIG. 4A.

When imaging this area with a fluorescence microscope, the image that is actually obtain by the fluorescence microscope is this distribution $F_0(x,y)$, convoluted with the resolution function of the microscope. In this example, the resolution function is schematically indicated as a circle 42 in FIG. 4A. When moving along the line A-B the resulting fluorescence signal from the microscope S(X,Y) will show a distribution 42', as shown in FIG. 4B.

When the whole area is illuminated with a dose d [C/m$^2$] of charged particles, the fluorescence changes and this changing fluorescence can be described as:

$$F(d,x,y) = q(d) \cdot F_0(x,y)$$

wherein q(d) may be a non-linear function of the dose of charged particles. When, for example, the fluorescence is quenched, q(d) decreases with d because at some point all the fluorescence is switched off. For small doses d, the function q can be approximated by:

$$q(d) = 1 - r \cdot d$$

where r is a decay rate.

Figure 5A:
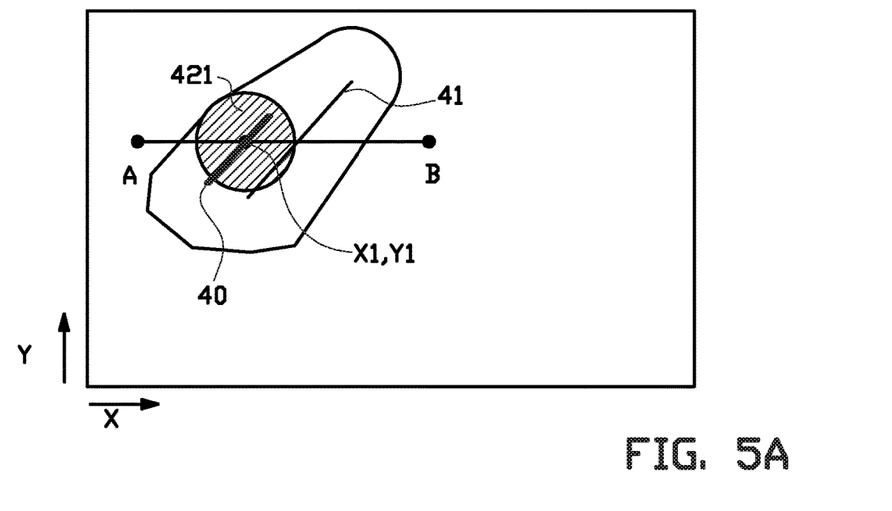
FIG. 5A schematically shows the changed of the fluorescence image when a charged particle beam is pointed at a position containing fluorescent markers.
Figure 5B:
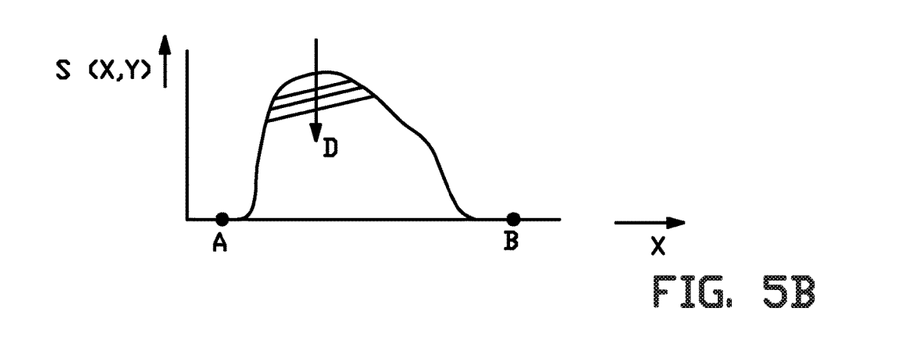
FIG. 5B schematically shows a fluorescence signal as a function of the position along the line A-B in FIG. 5A.
Figure 5C:
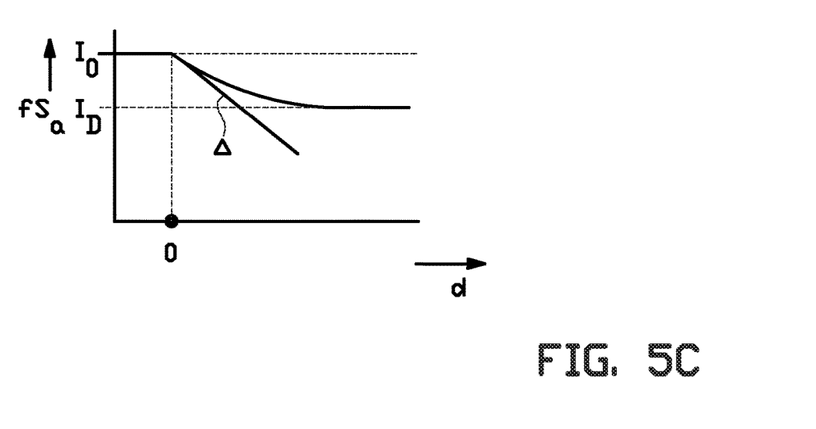
FIG. 5C schematically shows a fluorescence signal as a function of the dose of charged particles at the position X1,Y1 in FIG. 5A.

When only one point X1,Y1 on a position on the sample with markers 40 is irradiated with a dose of charged particles, as schematically shown in FIG. 5A, the fluorescence changes only at that point. Because of the limited resolution of the fluorescence microscope, this will have an effect within an area 421 equal to the resolution as shown in FIG. 5A. Other parts of the area 421 can contribute to the fluorescence signal $fS_a$, which other parts are not irradiated by the charged particles. At the point X1,Y1 the measured fluorescence $fS_a$ as a function of dose d, will not go to zero because there are other markers around the point X1,Y1 and within the area 421 equal to the resolution, that contribute to the measured fluorescence signal at X1,Y1 as schematically shown in FIGS. 5B and 5C. The fluorescence image S(X,Y) develops a "dip" D as schematically shown in FIG. 5B. The final decrease $I_D$ of the fluorescence intensity $fS_a$ is proportional to the number density or number concentration of markers in the irradiated position X1,Y1.

Figure 6A:
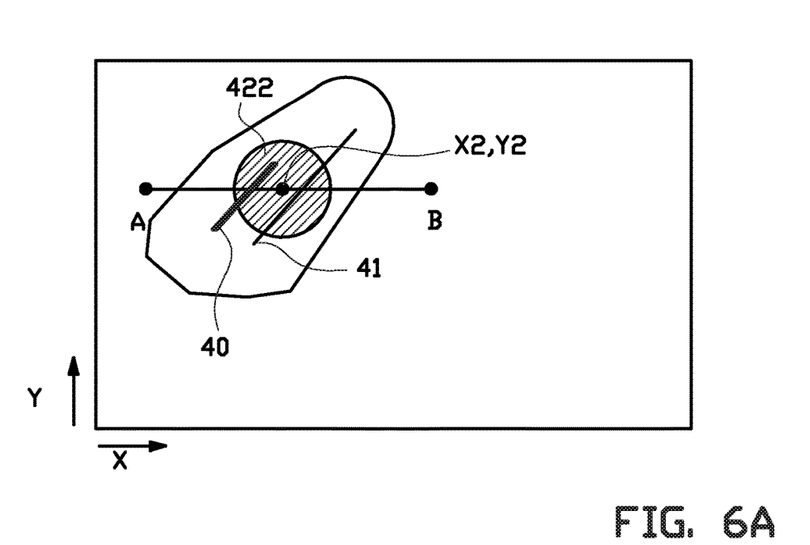
FIG. 6A schematically shows the changed of the fluorescence image when a charged particle beam is pointed at a position without fluorescent markers.
Figure 6B:
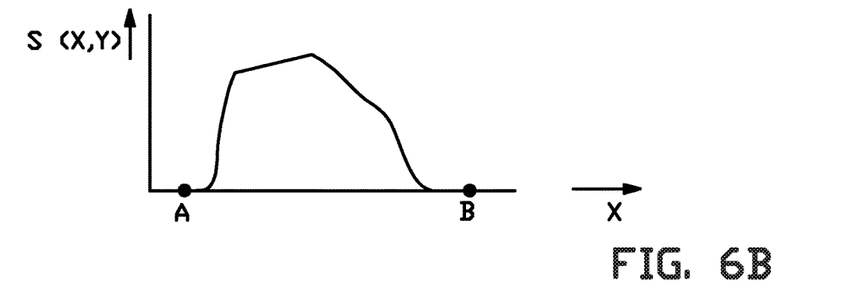
FIG. 6B schematically shows a fluorescence signal as a function of the position along the line A-B in FIG. 6A.
Figure 6C:
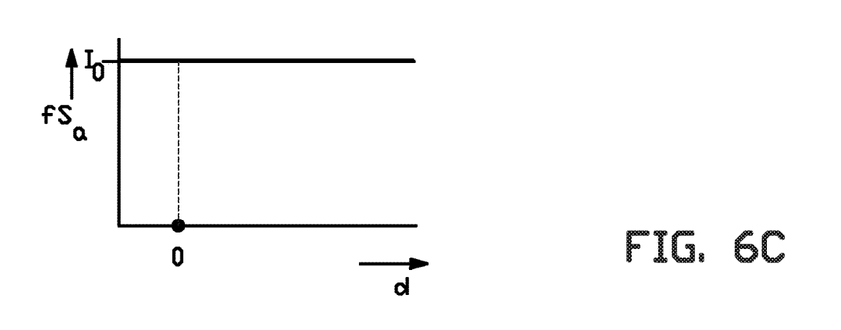
FIG. 6C schematically shows a fluorescence signal as a function of the dose of charged particles at the position X2,Y2 in FIG. 6A.

When subsequently a second point X2,Y2 on a position on the sample without markers is illuminated with a dose of charged particles, as depicted in FIG. 6A, the markers around the point X2,Y2 and within the area 422 equal to the resolution, will contribute to the measured signal S(X,Y). In this case, however, the measured fluorescence $fS_a$ as a function of the dose d at point X2,Y2 will remain substantially constant as schematically shown in FIGS. 6B and 6C.

Instead of measuring the depth, it is also possible to measure the rate of change of signal in the dip:

$$S(d+\partial d) - S(d) = -r \cdot \partial d \cdot F_0(x,y)$$

To obtain an image, the density must be measured at many points. If the charged particle beam is scanned over the sample, at each pixel of the image a certain dose d is deposited and a change in fluorescence $fS_a$ in the area around the particle beam can be determined and contributed to the pixel position of the particle beam. Thus, a whole image can be built up with the resolution of the charged particle beam.

As schematically indicated in FIG. 5C, a derivative Δ of the fluorescence signal $fS_a$ as a function of the deposited dose d of charged particles can be determined. Said derivative Δ provides a measure for the density of markers at the location X1,Y1 of the charged particle beam. Preferably, the derivative Δ is determined at or shortly after the onset of irradiating the location X1,Y1 with charged particles, as indicated in FIG. 5C. In this situation the derivative Δ, and thus a measure for the density of markers, can be determined without having to destroy all markers in said location X1,Y1.

In a substantial constant current of charged particles is used, the dose d is proportional with the irradiation time of location X1,Y1. In this case, the measure for the density of markers at said location X1,Y1 can also be obtained by determining the derivative of the fluorescence signal $fS_a$ as a function of time.

Example of the Method of the Invention for Making an Image Using a Wide Field Camera When using a wide field camera 4', as for example shown in the setup of FIG. 2, the position where a possible change of the fluorescence signal may be detectable moves with the position of the charged particle beam. When the charged particle beam irradiates a position containing a concentration of emitters, the fluorescence signal of these emitters changes as a function of the dose of charged particles. Due to this change the fluorescence image develops a local "dip" in case the fluorescence decreases or a local "peak" in case the fluorescence increases due to the irradiation by the dose of charged particles. In order to increase the signal-to-noise ratio, only the pixels of the camera 4' which image the "dip" or "peak" are used to measure the change in fluorescence. It is even possible to give the pixels in the center of the "dip" or "peak" more weight in the calculation than the pixels at the edge.

In addition or alternatively, when the charged particle beam moves from point to point, a reference image can be obtained to which the image with changing intensity in the "dip" or "peak" can be compared. When the charged particle beam scans over the sample, filter function can be applied to the wide field image, preferably centered around the position of the charged particle beam in the wide field image, and the total intensity in the filtered image is determined. The filter function thus selects the part of the wide field image from which the intensity is evaluated to determine the effect of the charged particle beam at its position. For example, the filter function typically has the size of the circle 42 determined by the resolution function of the microscope. In addition the filter function can also contain additional weigh-factors for each pixel.

Clearly, it is very important to know the position of the charged particle beam in the wide field image very precisely, because when the charged particle beam moves, the position where the fluorescence may change also moves. So for a perfect measurement it is preferred to determine the intensity in the appropriately filtered image before and after the deposition of the dose.

In an embodiment, however, the position of the charged particle beam shifts during the deposition of the dose. In this case, also the filter function shifts with the position of the charged particle beam. When determining the intensity in the appropriately filtered image before and after the deposition of the dose, an intensity changed due to the corresponding shift of the filter may be included. Thus, each original image must give two intensity values obtained with a slightly shifted filter function. One value is used as the 'post-dose intensity' for charged particle beam position x, and the other value is used as the 'pre-dose intensity' for position x+Δx. If this is not done, but instead only one filter position is used, a single intensity function for each position of the charged particle beam and thus a single image is obtained. In that case, the fluorescence density is simply obtained by differentiating this function with respect to the scan direction. However, the result contains a 'shadow' of the differentiated original fluorescence image.

Figure 7:
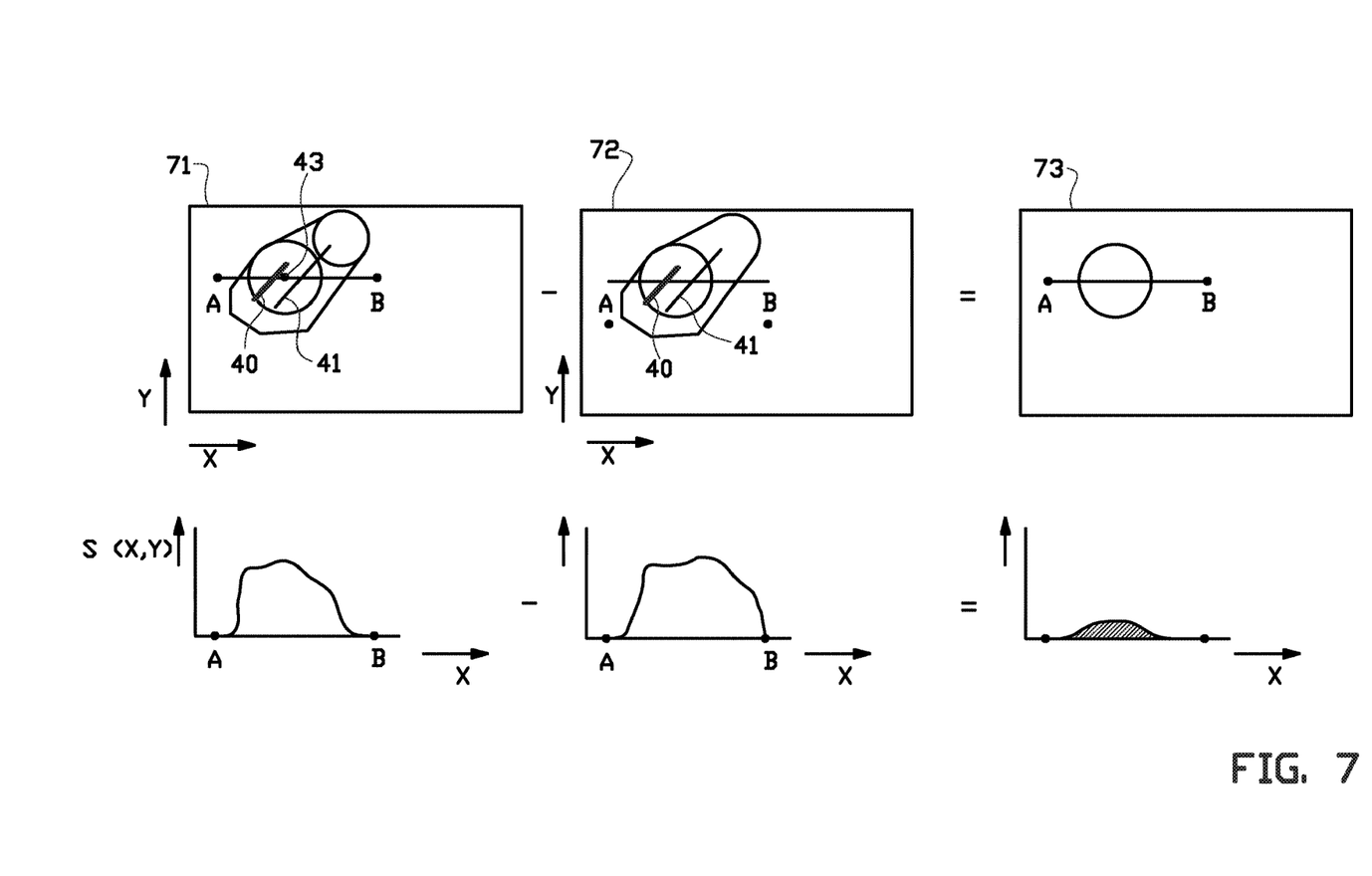
FIG. 7 schematically depicts two images obtained before and after exposure with a charged particle beam, which are subtracted to obtain a difference image.

Alternatively, two subsequent wide field images are obtained, a first image 72 with the charged particle beam 'off' and a subsequent second image 71 with the charged particle beam 43 'on'. These images 71, 72 are subtracted and the filter function is applied to the difference image 73 (FIG. 7).

A typical filter function may have the shape of the wide field resolution function. Because the filter function has the typical size of the optical resolution (or point spread function of a fluorescent marker), a wide field image may contain many filter functions: typically a distance apart of twice the resolution. The charged particle beam can deposit a dose in the center of all these filter functions between each read-out of the wide field image. In this way, it is possible to speed up the data acquisition considerably. For a super resolution image of 1000×1000 pixels with a resolution enhancement of a factor 10 with respect to the fluorescence image, the wide field resolution function is 10×10 pixels in the super resolution image. Thus, we may fit $(1000/40)2=625$ filter functions in the wide field image. This is the enhancement factor in the data acquisition.

Example of the Method of the Invention for Making an Image Using a Confocal Microscope In a confocal microscope as for example shown in the set-up of FIG. 1, the sample 10 is illuminated by a focused light beam. The fluorescence 12 is detected through an aperture 3 positioned in a conjugate plane of the sample 10. The alignment of the microscope is usually such that the aperture image on the sample 10 is centered with respect to the illuminated region. The electron beam 9 is then focused in the center of the illumination/detection region. Just as in the wide field case, for a measurement it is necessary to measure the signal at a particular location as a function of electron dose. An image is formed by repeating this measurement for many positions of the illumination/detection/electron-beam combination. However, it is preferable to keep the position of the illumination/detection region very stable on the sample during the measurement at one point, because a change in fluorescence signal resulting from a small movement may be many times greater than the change caused by the electron dose. In other words, the scan is preferably not continuous as in regular confocal microscopy but stops during data collection.

A first alternative method to such a 'stop-and-go' method above, is to keep the position of the illumination/detection region fixed for a while, and scan the electron beam over an area a×a in the center of this region to collect n×n pixels. Subsequently, the position of the illumination/detection region is moved over a distance a and the next set of n×n pixels is collected.

A second alternative method is to first collect a confocal fluorescent image while the electron beam is off. The confocal microscope is zoomed to the area where a super resolution image is desired and a scan is made with very small pixels, for instance 1000×1000 pixels of 10 nm. This provides a first image with a resolution that is low compared to the pixel size. This image presents the change in fluorescence signal resulting from a movement of the illumination/detection region. Subsequently, the electron beam is directed to the center of said illumination/detection region and a second image is collected while the electron beam deposits a dose d at the position of each pixel. This second image can be obtained either by scanning the illumination/detection region and the position of the electron beam together over the sample, or by scanning the sample mechanically through the combination of illumination/detection region plus electron beam. When stepping from one pixel to the next to obtain the second image, the fluorescence may drop for two reasons:

1. The fluorescence may drop due to a change in fluorescence signal resulting from a movement of the illumination/detection region. Such a change is substantially the same as in the first image.

2. The fluorescence may drop because the electron beam has bleached emitters in said pixel.

Now, if the fluorescence signal is differentiated with respect to the scan direction in order to get the rate of change in the fluorescence image that is proportional to the local marker concentration, there is a 'shadow' of the derivative of the original first picture. This shadow has a much lower resolution then our super resolution image and can easily be subtracted.

A small variation in this method is to perform the procedure line by line.

As in the wide field method, it is advisable to collect several images with relatively small changes to the sample in order to optimize the signal-to-noise in the final image that is obtained by combining the information from these several images.

It is to be understood that the above description is included to illustrate the operation of the preferred embodiments and is not meant to limit the scope of the invention. From the above discussion, many variations will be apparent to one skilled in the art that would yet be encompassed by the spirit and scope of the present invention.

The invention claimed is:

1. Method of determining a measure of a density of markers in a sample, comprising the steps of:
   irradiating an illumination region of the sample with light, wherein the markers present in the illumination region of the sample emit fluorescence light in response to the irradiation of the sample with light,
   detecting an intensity of the fluorescence light from a detection region of the sample, comprising at least a part of said the illumination region,
   irradiating an area within said detection region of the sample with a focused charged particle beam to deposit a dose of charged particles in said area,
   monitoring a change of the intensity of the fluorescent light in said area, and
   determining a measure of the density of markers in said area using the change of the detected intensity of the fluorescence light as a function of the deposited dose of charged particles in said area.

2. Method according to claim 1, wherein the measure for the density of markers at said location is obtained by determining the derivative of the fluorescence signal as a function of the deposited dose of charged particles.

3. Method according to claim 1, wherein the measure of the density of markers in said area is determined using a rate of change of the intensity of the fluorescence light, in combination with depositing a constant current of charged particles.

4. Method according to claim 3, wherein the measure for the density of markers at said location is obtained by determining the derivative of the fluorescence signal as a function of time.

5. Method according to claim 1, wherein the detection region is centered around the area irradiated by the focused charged particle beam.

6. Method according to claim 1, wherein the focused charged particle beam is scanned over at least a part of the sample, wherein at multiple positions in said at least a part of the sample a measure of the density of marker is determined, and wherein said measure of the density as determined at said multiple positions is used to produce an image of the density distribution of said markers in said part of the sample.

7. Method according to claim 6, wherein the part of the sample is arranged within said detection region, and wherein during said scanning, the intensity of the fluorescence light is detected from the same detection region of the sample.

8. Method according to claim 6, wherein a center of the detection region on the sample is scanned together with the focused charged particle beam.

9. Method according to claim 6, wherein the scanning is repeated to obtain subsequent scans, wherein for each scan the intensity of the fluorescence light is measured once per position of the charged particle beam, wherein each measurement represents the effect of deposition of a constant dose per position, wherein the measurements of the subsequent scans are combined to produce an image of the density distribution of said markers in said part of the sample.

10. Method according to claim 6, wherein the scanning is repeated to obtain subsequent scans, wherein for each scan the intensity of the fluorescence light is measured once per position of the charged particle beam and is used to produce one image per scan, wherein said image represents the effect of deposition of a constant dose per position in said image, wherein said images of the subsequent scans are combined to produce an image of the density distribution of said markers in said part of the sample.

11. Method according to claim 1, wherein a position of the sample where a dose of charged particles is deposited and where the change in the intensity of the fluorescence light is measured, is selected based on the intensity of the fluorescence light as measured before a dose of charged particles is deposited.

12. Method according to claim 1, wherein the detection region in which the intensity of the fluorescence light is measured is scanned over at least a part of the sample, wherein a first scan is obtained without the charged particle beam irradiating the sample and a second scan is obtained with the charged particle beam irradiating the sample, and wherein variations in the intensity of the fluorescent light as measured during the scanning of the detection region in the first scan are used to compensate for variations in the intensity of the fluorescent light as measured during the scanning of the detection region in the second scan.

13. Method according to claim 12, wherein variations in the intensity of the fluorescent light as measured during the scanning of the detection region in the first scan are subtracted from the intensity of the fluorescent light as measured during the scanning of the detection region in the second scan.

14. Method according to claim 1, in which the sample is imaged onto a pixelated detector or camera, in particular a CCD camera or a CMOS camera, and wherein said detecting an intensity of the fluorescence light from a detection region of the sample is obtained by filtering the image information from said detector or camera in order to obtain only information from the detection region.

15. Method according to claim 14, wherein the position of the focused charged particle beam on the sample is stationary between two subsequent read outs of said detector or camera.

16. Method according to claim 14, wherein the position of the focused charged particle beam is varied over multiple separate positions on the sample between two subsequent read outs of said detector or camera, wherein a separation between said separate positions on the sample is equal or larger than the size of said detection region.

17. Method according to claim 1, wherein the intensity of the fluorescence light is measured through an aperture in a conjugate plane of the sample.

18. Method according to claim 1, wherein a size and/or position of illumination region on the sample is determined by an aperture in a conjugate plane of the sample.

19. A computer program having instructions adapted to construct an image of a distribution of markers in a sample provided with said markers, wherein said image is constructed using or calculating a measure of the density of the markers at various locations in or on said sample using the methods according to claim 1.

20. A computer readable medium, having a computer program according to claim 19 recorded thereon.

21. Inspection apparatus for determining a measure of a density of markers in a sample, said inspection apparatus comprising in combination:
- an optical microscope arranged for irradiating an illumination region of the sample with light, wherein the markers present in the illumination region of the sample emit fluorescence light in response to the irradiation of the sample with light, and for detecting an intensity of the fluorescence light from a detection region of the sample, wherein said detection region comprising at least a part of said illumination region;
- an ion- or electron microscope arranged for irradiating an area within said detection region of the sample with a focused charged particle beam; and
- a data processing system adapted to construct an image of a distribution of markers in the sample, wherein said image is constructed using or calculating a measure of the density of the markers at various locations in or on said sample as obtained using the method according to claim 1.

22. Method of determining a measure of a density of markers in a sample, comprising the steps of:
- irradiating an illumination region of the sample with light, wherein the markers present in the illumination region of the sample emit fluorescence light in response to the irradiation of the sample with light,
- detecting an intensity of the fluorescence light from a detection region of the sample, comprising at least a part of said the illumination region,
- irradiating an area within said detection region of the sample with a focused charged particle beam to deposit a dose of charged particles in said area,
- monitoring a change of the intensity of the fluorescent light in said area, and
- determining a measure of the density of markers in said area using the change of the detected intensity of the fluorescence light as a function of the deposited dose of charged particles in said area, wherein the detection region in which the intensity of the fluorescence light is measured is scanned over at least a part of the sample, wherein a first scan is obtained without the charged particle beam irradiating the sample and a second scan is obtained with the charged particle beam irradiating the sample, and wherein variations in the intensity of the fluorescent light as measured during the scanning of the detection region in the first scan are used to compensate for variations in the intensity of the fluorescent light as measured during the scanning of the detection region in the second scan.

* * * * *